United States Patent
Sartor (10) Patent No.: US 8,100,902 B2
(45) Date of Patent: *Jan. 24, 2012

(54) ELECTRODE WITH ROTATABLY DEPLOYABLE SHEATH

(75) Inventor: Joe Don Sartor, Longmont, CO (US)

(73) Assignee: Covidien AG (CH)

( * ) Notice: Subject to any disclaimer, the term of this patent is extended or adjusted under 35 U.S.C. 154(b) by 203 days.

This patent is subject to a terminal disclaimer.

(21) Appl. No.: 12/363,322

(22) Filed: Jan. 30, 2009

(65) Prior Publication Data

US 2009/0138012 A1     May 28, 2009

Related U.S. Application Data

(63) Continuation of application No. 11/168,901, filed on Jun. 28, 2005, now Pat. No. 7,500,974.

(51) Int. Cl.
*A61B 18/14* (2006.01)
(52) U.S. Cl. ............................. 606/45; 606/49
(58) Field of Classification Search .................. 606/45, 606/49
See application file for complete search history.

(56) References Cited

U.S. PATENT DOCUMENTS

| | | | |
|---|---|---|---|
| 3,460,539 A | 8/1969 | Anhalt, Sr. |
| 3,825,004 A | 7/1974 | Durden, III |
| 3,828,780 A | 8/1974 | Morrison, Jr. |
| 3,875,945 A | 4/1975 | Friedman |
| 3,902,494 A | 9/1975 | Haberlen et al. |
| 3,906,955 A | 9/1975 | Roberts |
| 3,967,084 A | 6/1976 | Pounds |
| 3,974,833 A | 8/1976 | Durden, III |
| 4,032,738 A | 6/1977 | Esty et al. |
| 4,034,761 A | 7/1977 | Prater et al. |
| D253,247 S | 10/1979 | Gill |
| 4,232,676 A | 11/1980 | Herczog |
| 4,314,559 A | 2/1982 | Allen |
| 4,427,006 A | 1/1984 | Nottke |
| 4,443,935 A | 4/1984 | Zamba et al. |
| 4,459,443 A | 7/1984 | Lewandowski |
| 4,463,234 A | 7/1984 | Bennewitz |
| 4,463,759 A | 8/1984 | Garito et al. |
| 4,492,231 A | 1/1985 | Auth |

(Continued)

FOREIGN PATENT DOCUMENTS

DE     30 45 996     7/1982

(Continued)

OTHER PUBLICATIONS

International Search Report from PCT/US03/37111.

(Continued)

*Primary Examiner* — Lee S Cohen (57) ABSTRACT

A sheath system for selectively covering a distal end of an electrocautery blade is provided. The sheath system includes a hub having a body portion defining a lumen therethrough and a sheath having a body portion defining a lumen therethrough. The lumen of the sheath is configured and dimensioned to operatively receive an electrocautery blade therein. The sheath is translatably associated with the hub such that rotation of the hub in a first direction results in axial movement of the sheath in a first direction to expose a distal end of the electrocautery blade and rotation of the hub in a second direction, opposite to the first direction, results in axial movement of the sheath in a second direction to cover the distal end of the electrocautery blade. The hub and the sheath may be concentric with one another.

16 Claims, 7 Drawing Sheets

U.S. PATENT DOCUMENTS

| | | |
|---|---|---|
| 4,545,375 A | 10/1985 | Cline |
| 4,562,838 A | 1/1986 | Walker |
| 4,589,411 A | 5/1986 | Friedman |
| 4,619,258 A | 10/1986 | Pool |
| 4,625,723 A | 12/1986 | Altnether et al. |
| 4,640,279 A | 2/1987 | Beard |
| 4,642,128 A | 2/1987 | Solorzano |
| 4,655,215 A | 4/1987 | Pike |
| 4,657,016 A | 4/1987 | Garito et al. |
| 4,683,884 A | 8/1987 | Hatfield et al. |
| 4,688,569 A | 8/1987 | Rabinowitz |
| 4,701,193 A | 10/1987 | Robertson et al. |
| 4,735,603 A | 4/1988 | Goodson et al. |
| 4,754,754 A | 7/1988 | Garito et al. |
| 4,785,807 A | 11/1988 | Blanch |
| 4,790,312 A | 12/1988 | Capuano, Sr. et al. |
| 4,827,911 A | 5/1989 | Broadwin et al. |
| 4,846,790 A | 7/1989 | Hornlein et al. |
| 4,850,353 A | 7/1989 | Stasz et al. |
| 4,862,890 A | 9/1989 | Stasz et al. |
| 4,869,715 A | 9/1989 | Sherburne |
| 4,886,060 A | 12/1989 | Wiksell |
| 4,901,719 A | 2/1990 | Trenconsky et al. |
| 4,909,249 A | 3/1990 | Akkas et al. |
| 4,911,159 A | 3/1990 | Johnson et al. |
| 4,916,275 A | 4/1990 | Almond |
| 4,921,476 A | 5/1990 | Wuchinich |
| 4,931,047 A | 6/1990 | Broadwin et al. |
| 4,986,839 A | 1/1991 | Wertz et al. |
| 4,988,334 A | 1/1991 | Hornlein et al. |
| 5,015,227 A | 5/1991 | Broadwin et al. |
| 5,026,368 A | 6/1991 | Adair |
| 5,055,100 A | 10/1991 | Olsen |
| 5,071,418 A | 12/1991 | Rosenbaum |
| 5,076,276 A | 12/1991 | Sakurai et al. |
| 5,088,997 A | 2/1992 | Delahuerga et al. |
| 5,098,430 A | 3/1992 | Fleenor |
| 5,100,402 A | 3/1992 | Fan |
| 5,133,714 A | 7/1992 | Beane |
| 5,147,292 A | 9/1992 | Kullas et al. |
| D330,253 S | 10/1992 | Burek |
| 5,160,334 A | 11/1992 | Billings et al. |
| 5,162,044 A | 11/1992 | Gahn et al. |
| 5,178,605 A | 1/1993 | Imonti |
| 5,190,517 A | 3/1993 | Zieve et al. |
| 5,192,267 A | 3/1993 | Shapira et al. |
| 5,195,959 A | 3/1993 | Smith |
| 5,196,007 A | 3/1993 | Ellman et al. |
| 5,197,962 A | 3/1993 | Sansom et al. |
| 5,199,944 A | 4/1993 | Cosmescu |
| 5,217,457 A | 6/1993 | Delahuerga et al. |
| 5,224,944 A | 7/1993 | Elliott |
| 5,226,904 A | 7/1993 | Gentelia et al. |
| 5,233,515 A | 8/1993 | Cosman |
| 5,234,428 A | 8/1993 | Kaufman |
| 5,242,442 A | 9/1993 | Hirschfeld |
| 5,244,462 A | 9/1993 | Delahuerga et al. |
| 5,246,440 A | 9/1993 | Van Noord |
| 5,254,082 A | 10/1993 | Takase |
| 5,254,117 A | 10/1993 | Rigby et al. |
| 5,256,138 A | 10/1993 | Burek et al. |
| 5,269,781 A | 12/1993 | Hewell, III |
| 5,300,087 A | 4/1994 | Knoepfler |
| 5,304,763 A | 4/1994 | Ellman et al. |
| 5,306,238 A | 4/1994 | Fleenor |
| 5,312,329 A | 5/1994 | Beaty et al. |
| 5,318,516 A | 6/1994 | Cosmescu |
| 5,318,565 A | 6/1994 | Kuriloff et al. |
| 5,334,183 A | 8/1994 | Wuchinich |
| 5,342,356 A | 8/1994 | Ellman et al. |
| 5,348,555 A | 9/1994 | Zinnanti |
| 5,376,089 A | 12/1994 | Smith |
| 5,380,320 A | 1/1995 | Morris |
| 5,382,247 A | 1/1995 | Cimino et al. |
| 5,395,363 A | 3/1995 | Billings et al. |
| 5,399,823 A | 3/1995 | McCusker |
| 5,401,273 A | 3/1995 | Shippert |
| 5,403,882 A | 4/1995 | Huggins |
| 5,406,945 A | 4/1995 | Riazzi et al. |
| 5,409,484 A | 4/1995 | Erlich et al. |
| 5,413,575 A | 5/1995 | Haenggi |
| 5,421,829 A | 6/1995 | Olichney et al. |
| 5,431,650 A | 7/1995 | Cosmescu |
| 5,451,222 A | 9/1995 | De Maagd et al. |
| 5,460,602 A | 10/1995 | Shapira |
| 5,462,522 A | 10/1995 | Sakurai et al. |
| 5,484,398 A | 1/1996 | Stoddard |
| 5,484,434 A | 1/1996 | Cartmell et al. |
| 5,486,162 A | 1/1996 | Brumbach |
| 5,498,654 A | 3/1996 | Shimasaki et al. |
| 5,531,722 A | 7/1996 | Van Hale |
| 5,549,604 A | 8/1996 | Sulcu et al. |
| 5,601,224 A | 2/1997 | Bishop et al. |
| 5,609,573 A | 3/1997 | Sandock |
| 5,634,912 A | 6/1997 | Injev |
| 5,643,256 A | 7/1997 | Urueta |
| 5,669,907 A | 9/1997 | Platt, Jr. et al. |
| 5,693,050 A | 12/1997 | Speiser |
| 5,693,052 A | 12/1997 | Weaver |
| 5,697,926 A | 12/1997 | Weaver |
| 5,702,360 A | 12/1997 | Dieras et al. |
| 5,702,387 A | 12/1997 | Arts et al. |
| 5,713,895 A | 2/1998 | Lontine et al. |
| 5,720,745 A | 2/1998 | Farin et al. |
| D393,067 S | 3/1998 | Geary et al. |
| 5,765,418 A | 6/1998 | Rosenberg |
| 5,776,092 A | 7/1998 | Farin et al. |
| 5,792,139 A | 8/1998 | Chambers et al. |
| 5,797,907 A | 8/1998 | Clement |
| 5,827,280 A | 10/1998 | Sandock et al. |
| 5,836,897 A | 11/1998 | Sakurai et al. |
| D402,030 S | 12/1998 | Roberts et al. |
| D402,031 S | 12/1998 | Roberts et al. |
| 5,843,109 A | 12/1998 | Mehta et al. |
| 5,868,768 A | 2/1999 | Wicherski et al. |
| 5,893,862 A | 4/1999 | Pratt et al. |
| 5,941,887 A | 8/1999 | Steen et al. |
| 5,944,737 A | 8/1999 | Tsonton et al. |
| 5,951,581 A | 9/1999 | Saadat et al. |
| 5,972,007 A | 10/1999 | Sheffield et al. |
| 6,004,318 A | 12/1999 | Garito et al. |
| 6,004,333 A | 12/1999 | Sheffield et al. |
| 6,063,050 A | 5/2000 | Manna et al. |
| 6,070,444 A | 6/2000 | Lontine et al. |
| 6,099,525 A | 8/2000 | Cosmescu |
| 6,117,134 A | 9/2000 | Cunningham et al. |
| 6,139,547 A | 10/2000 | Lontine et al. |
| 6,142,995 A | 11/2000 | Cosmescu |
| 6,146,353 A | 11/2000 | Platt, Jr. |
| D441,077 S | 4/2001 | Garito et al. |
| 6,213,999 B1 | 4/2001 | Platt, Jr. et al. |
| 6,249,706 B1 | 6/2001 | Sobota et al. |
| 6,251,110 B1 | 6/2001 | Wampler |
| 6,257,241 B1 | 7/2001 | Wampler |
| 6,258,088 B1 | 7/2001 | Tzonev et al. |
| 6,287,344 B1 | 9/2001 | Wampler et al. |
| 6,312,441 B1 | 11/2001 | Deng |
| D453,222 S | 1/2002 | Garito et al. |
| 6,358,281 B1 | 3/2002 | Berrang et al. |
| 6,361,532 B1 | 3/2002 | Burek |
| 6,402,748 B1 | 6/2002 | Schoenman et al. |
| 6,494,882 B1 | 12/2002 | Lebouitz et al. |
| 6,747,218 B2 | 6/2004 | Huseman et al. |
| D493,530 S | 7/2004 | Reschke |
| D493,888 S | 8/2004 | Reschke |
| D494,270 S | 8/2004 | Reschke |
| D495,051 S | 8/2004 | Reschke |
| D495,052 S | 8/2004 | Reschke |
| 7,500,974 B2 * | 3/2009 | Sartor .................. 606/45 |
| 2003/0004508 A1 | 1/2003 | Morgan et al. |
| 2004/0010248 A1 | 1/2004 | Appling et al. |
| 2004/0092927 A1 | 5/2004 | Podhajsky et al. |
| 2004/0230262 A1 | 11/2004 | Sartor et al. |

FOREIGN PATENT DOCUMENTS

| | | |
|---|---|---|
| EP | 1050277 | 11/2000 |
| EP | 1050279 | 11/2000 |
| EP | 1082945 | 3/2001 |
| EP | 1293171 | 3/2003 |
| FR | 2235669 | 1/1975 |
| WO | WO 94/20032 | 9/1994 |
| WO | WO 01/64122 | 9/2001 |

OTHER PUBLICATIONS

International Search Report from PCT/US04/04685.
International Search Report from EP/0401/5980.
International Search Report from PCT/US03/22900.

* cited by examiner

ELECTRODE WITH ROTATABLY DEPLOYABLE SHEATH

CROSS-REFERENCE TO RELATED APPLICATION

The present application is a Continuation application claiming the benefit of and priority to U.S. application Ser. No. 11/168,901, now U.S. Pat. No. 7,500,974, filed on Jun. 28, 2005, the entire content of which is incorporated herein by reference.

BACKGROUND

1. Technical Field

The present disclosure relates generally to electrosurgical instruments and, more particularly, to an electrode including a selectively deployable protective sheath.

2. Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical cutting and fulguration.

In particular, electrosurgical fulguration includes the application of electric spark to biological tissue, for example, human flesh or the tissue of internal organs, without significant cutting. The spark is produced by bursts of radio-frequency electrical or electrosurgical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical pencil" is intended to include instruments which have a handpiece which is attached to an active electrode and which is used to cauterize, coagulate and/or cut tissue. Typically, the electrosurgical pencil may be operated by a handswitch or a foot switch. The active electrode is an electrically conducting element which is usually elongated and may be in the form of a thin flat blade with a pointed or rounded distal end. Alternatively, the active electrode may include an elongated narrow cylindrical needle which is solid or hollow with a flat, rounded, pointed or slanted distal end. Typically electrodes of this sort are known in the art as "blade", "loop" or "snare", "needle" or "ball" electrodes.

As mentioned above, the handpiece of the electrosurgical pencil is connected to a suitable electrosurgical energy source (i.e., generator) which produces the radio-frequency electrical energy necessary for the operation of the electrosurgical pencil. In general, when an operation is performed on a patient with an electrosurgical pencil, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue, and a blend wave form tends to be somewhere between a cut and coagulate wave from. The power or energy parameters are typically controlled from outside the sterile field which requires an intermediary like a circulating nurse to make such adjustment.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue.

In particular with the use of active electrodes having a sharpened or pointed tip, a need exists for electrosurgical instruments (i.e., electrosurgical pencils) including incorporated safety features, elements and/or systems to protect the user from inadvertent or accidental pricking and/or stabbing by the active electrode.

SUMMARY

According to an aspect of the present disclosure, a sheath system for selectively covering a distal end of an electrocautery blade is provided. The sheath system includes a hub having a body portion defining a lumen therethrough; and a sheath having a body portion defining a lumen therethrough. The lumen of the sheath is configured and dimensioned to operatively receive an electrocautery blade therein. The sheath is translatably associated with the hub such that rotation of the hub in a first direction results in axial movement of the sheath in a first direction to expose a distal end of the electrocautery blade and rotation of the hub in a second direction, opposite to the first direction, results in axial movement of the sheath in a second direction to cover the distal end of the electrocautery blade. It is envisioned that the hub and the sheath are concentric with one another.

The body portion of the hub may include at least one helical groove formed in an inner surface thereof. Meanwhile, the body portion of the sheath includes at least one nub extending from an outer surface thereof. The nub may be configured and dimensioned to slidably engage the groove of the hub. Accordingly, as the hub is rotated, the nub of the sheath rides along the helical groove of the hub to translate the sheath in one of a distal and proximal direction.

The sheath system further includes a collar configured and dimensioned to support the electrocautery blade. Each of a distal end and a proximal end of the electrocautery blade extends from a respective distal and proximal end of the collar. At least a portion of the collar is rotatably supported in the body portion of the hub and a portion of the collar is disposed in the lumen of the sheath. The collar may include an annular flange extending from an outer surface thereof, and the hub may include an annular groove formed in an inner surface of the body portion. As such, the annular groove of the hub is configured and dimensioned to slidably receive the annular flange of the collar.

It is envisioned that the body portion of the sheath may include an elongated slot formed therein and the collar may include a stub extending from the outer surface thereof. In an embodiment, the stub of the collar is configured and dimensioned to slidably engage the elongated slot formed in the body portion of the sheath. Accordingly, the inter-engagement of the stub of the collar in the elongate slot of the sheath prevents rotation of the sheath as the hub is rotated.

It is contemplated that at least a portion of each of the hub, the sheath and the connector is fabricated from non-conductive materials. It is further contemplated that the body portion of the hub includes finger grips.

According to another aspect of the present disclosure, a sheath system for selectively covering a distal end of an electrocautery blade is provided. The sheath system includes a hub having a body portion defining a lumen therethrough. The body portion of the hub includes a helical groove and an annular groove formed therein. The annular groove is formed at a location proximal of the helical groove.

The sheath system further includes a sheath having a body portion defining a lumen therethrough. The body portion of the sheath includes a nub extending from an outer surface thereof, wherein the nub is configured and dimensioned to slidably engage the helical groove formed in the hub; and an elongated slot formed therein. The sheath is translatably associated with the hub such that rotation of the hub in a first direction results in axial movement of the sheath in a first direction to expose a distal end of the electrocautery blade and rotation of the hub in a second direction, opposite to the first direction, results in axial movement of the sheath in a second direction to cover the distal end of the electrocautery blade.

The sheath system further includes a collar configured and dimensioned for support on the electrocautery blade. A distal end and a proximal end of the electrocautery blade each extend from a respective distal end and proximal end of the collar. It is envisioned that at least a portion of the collar is rotatably supported in the body portion of the hub and a portion of the collar is disposed in the lumen of the sheath. The collar desirably includes an annular flange extending from an outer surface thereof for slidable engagement in the annular groove formed in the hub; and a stub extending from the outer surface of thereof at a location distal of the annular flange for slidable engagement in the elongate slot of the sheath. Accordingly, rotation of the hub a first direction results in axial movement of the sheath in a first direction to expose a distal end of the electrocautery blade and rotation of the hub in a second direction, opposite to the first direction, results in axial movement of the sheath in a second direction to cover the distal end of the electrocautery blade.

It is envisioned that the hub, the sheath, and the collar are concentric with one another. It is contemplated that at least a portion of each of the hub, the sheath and the connector is fabricated from non-conductive materials. Desirably, the body portion of the hub includes finger grips.

In operation, as the hub is rotated, the nub of the sheath rides along the helical groove of the hub to translate the sheath in one of a distal and proximal direction. Additionally, the inter-engagement of the stub of the collar in the elongated slot of the sheath prevents the rotation of the sheath as the hub is rotated.

According to yet another aspect of the present disclosure, an electrosurgical pencil for electrical connection to an electrosurgical generator is provided. The electrosurgical pencil includes an elongate housing; an electrocautery blade including a proximal end supported in the housing, and a distal end extending distally from the housing, the electrocautery blade being electrically connectable with the electrosurgical generator; at least one activation switch supported on the housing, each activation switch being configured and adapted to selectively activate the electrosurgical pencil; and a sheath system for selectively covering and exposing the distal end of the electrocautery blade.

The sheath system includes a hub having a body portion defining a lumen therethrough; and a sheath including a body portion defining a lumen therethrough. The lumen of the sheath is configured and dimensioned to operatively receive the electrocautery blade therein. The sheath is translatably associated with the hub such that rotation of the hub in a first direction results in axial movement of the sheath in a first direction to expose the distal end of the electrocautery blade and rotation of the hub in a second direction, opposite to the first direction, results in axial movement of the sheath in a second direction to cover the distal end of the electrocautery blade.

In this embodiment, it is envisioned that the hub and the sheath are concentric with one another.

The body portion of the hub may include at least one helical groove formed in an inner surface thereof; and the body portion of the sheath desirably includes at least one nub extending from an outer surface thereof. It is envisioned that the nub is configured and dimensioned to slidably engage the groove of the hub. Accordingly, as the hub is rotated, the nub of the sheath rides along the helical groove of the hub to translate the sheath in one of a distal and proximal direction.

The sheath system further includes a collar configured and dimensioned for support on the electrocautery blade, wherein each of the distal end and the proximal end of the electrocautery blade extends from a respective distal and proximal end of the collar. At least a portion of the collar is rotatably supported in the body portion of the hub and at least a portion of the collar is disposed in the lumen of the sheath.

Desirably, the collar includes an annular flange extending from an outer surface thereof, and the hub desirably includes an annular groove formed in an inner surface of the body portion. It is envisioned that the annular groove of the hub is configured and dimensioned to slidably receive the annular flange of the collar.

Desirably, the body portion of the sheath includes an elongate slot formed therein, and the collar includes a stub extending from the outer surface thereof. It is envisioned that the stub of the collar is configured and dimensioned to slidably engage the elongate slot formed in the body portion of the sheath. In use, the inter-engagement of the stub of the collar in the elongate slot of the sheath prevents the rotation of the sheath as the hub is rotated.

According to still another aspect of the present disclosure, a sheath system for selectively covering a distal end of an electrocautery blade is provided. It is envisioned that the electrocautery blade may be electrically connectable to an electrosurgical device and may be capable of transmitting electrosurgical energy. The sheath system includes an electrocautery blade having a distal end and a proximal end; a collar configured and dimensioned for support on the electrocautery blade; a sheath operatively supported on a distal end of the collar; and a hub operatively supported on the sheath and on a proximal end of the collar.

Desirably, the distal end and the proximal end of the electrocautery blade each extend from a respective distal and proximal end of the collar. The collar includes an annular flange extending from an outer surface thereof; and a stub extending from the outer surface thereof at a location distal of the annular flange.

Desirably, the sheath includes a body portion defining a lumen therethrough; a nub extending from an outer surface of the body portion of the sheath; and an elongated slot formed in the body portion of the sheath for slidably receiving the stub of the collar therein.

Desirably, the hub includes a body portion defining a lumen therethrough. The body portion of the hub includes a helical groove formed therein for slidably engaging the nub of the collar and an annular groove formed therein for rotatably receiving the annular flange of the collar. The annular groove is formed at a location proximal of the helical groove.

Desirably, the sheath is translatably associated with the hub such that rotation of the hub in a first direction results in axial movement of the sheath in a first direction to expose a distal end of the electrocautery blade, and rotation of the hub in a second direction, opposite to the first direction, results in axial movement of the sheath in a second direction to cover the distal end of the electrocautery blade.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

Particular embodiments of the presently disclosed electrosurgical pencil and sheath system will now be described in detail with reference to the drawing figures wherein like reference numerals identify similar or identical elements. As used herein, the term "distal" refers to that portion which is further from the user while the term "proximal" refers to that portion which is closer to the user or surgeon.

Figure 1:
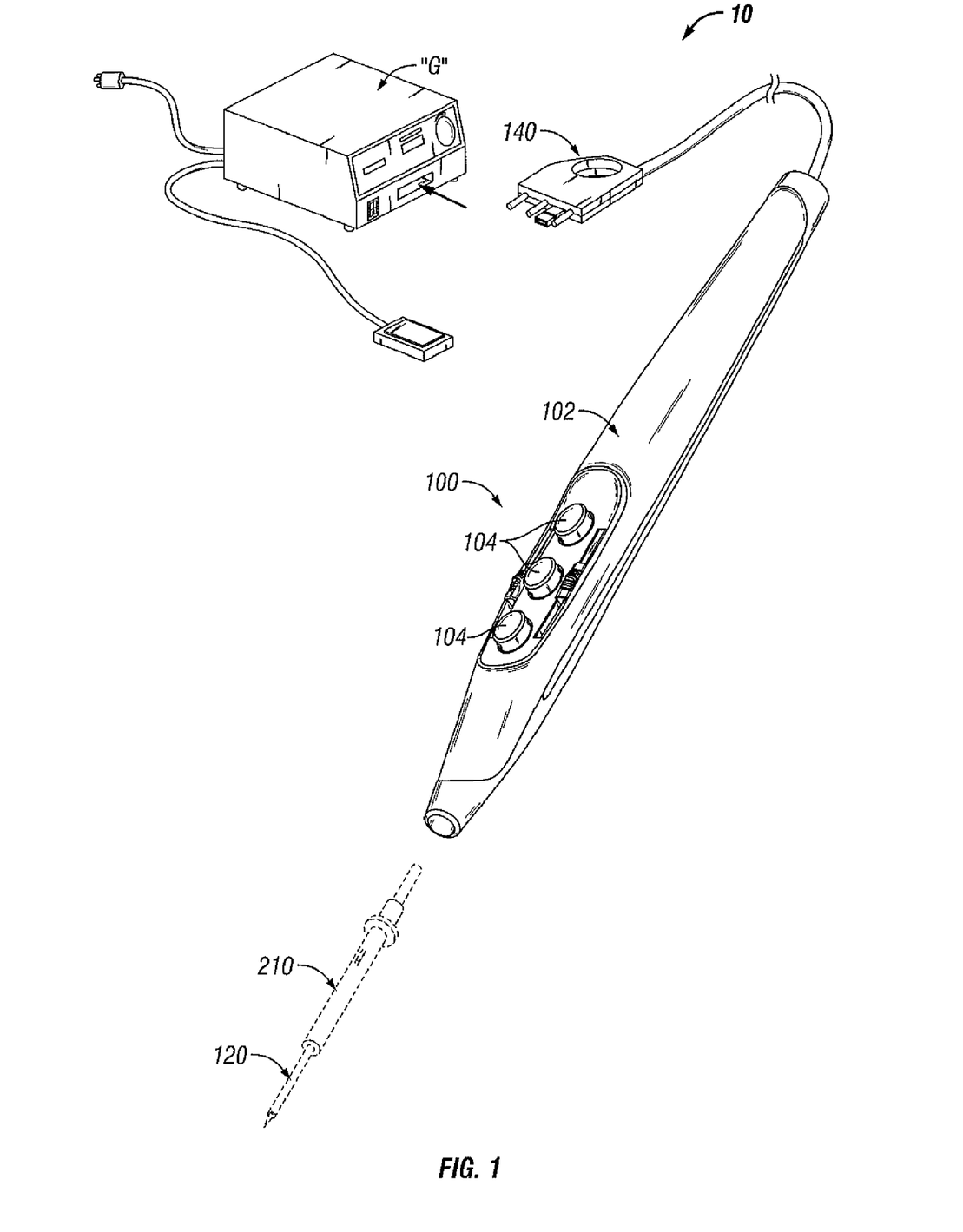
FIG. 1 is a perspective view of a typical electrosurgical system.

Referring initially to FIG. 1, there is seen a perspective view of an electrosurgical instrument system in accordance with an embodiment of the present disclosure, generally indicated as reference numeral 10. Electrosurgical instrument system 10 includes an electrosurgical instrument 100 constructed in accordance with an embodiment of the present disclosure. While the following description will be directed towards electrosurgical pencils including sharpened or pointed electrocautery blades and the like, it is envisioned that the features and concepts (or portions thereof) of the present disclosure can be applied to electrosurgical pencils including any type of electrocautery blade.

Electrosurgical pencil 100 includes a housing 102 configured and adapted to support a sheath system 200 (FIGS. 2-8) at a distal end thereof which, in turn, receives a replaceable electrode or electrocautery blade 120 therein. Electrosurgical pencil 100 further includes at least one activation button 104 supported on an outer surface of housing 102. Activation button(s) 104 are operable to control the supply of RF electrical energy to blade 120 from an electrosurgical generator "G". Electrosurgical pencil 100 may be coupled to electrosurgical generator "G" via a plug assembly 140.

Other electrosurgical pencils which may incorporate and/or include the sheath system disclosed herein are identified in U.S. patent application Ser. No. 10/959,824, filed on Oct. 6, 2004, entitled "Electrosurgical Pencil with Improved Controls"; and International Application No. PCT/US03/37111, filed on Nov. 20, 2003, also entitled "Electrosurgical Pencil with Improved Controls", the entire contents of each of which being incorporated by reference herein.

By way of example only, electrosurgical generator "G" may be any one of the following, or equivalents thereof: the "FORCE FX", "FORCE 2" or "FORCE 4" generators manufactured by Valleylab, Inc. of Boulder, Colo., a Division of Tyco Healthcare LP. It is contemplated that electrosurgical generator "G" can be preset to selectively provide an appropriate first predetermined RF signal (e.g., about 1 to 300 watts) for tissue cutting and an appropriate second predetermined RF signal (e.g., about 1 to 120 watts) for tissue coagulation. However, electrosurgical generator "G" may be adapted to automatically configure itself to transmit particular RF signals depending on the particular electrosurgical instrument connected thereto.

Figure 2:
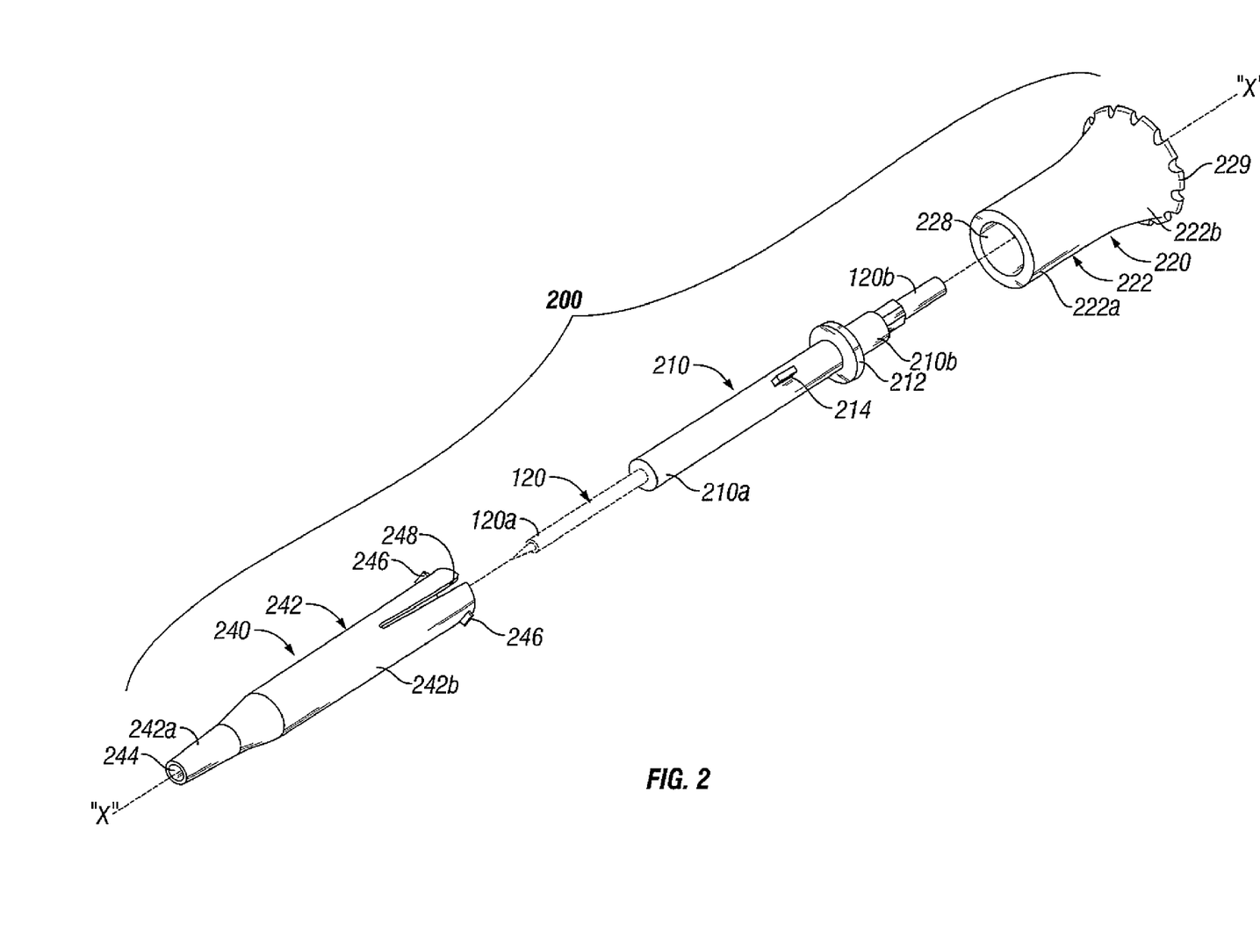
FIG. 2 is a perspective view, with parts separated, of the sheath system of FIG. 1.
Figure 3:
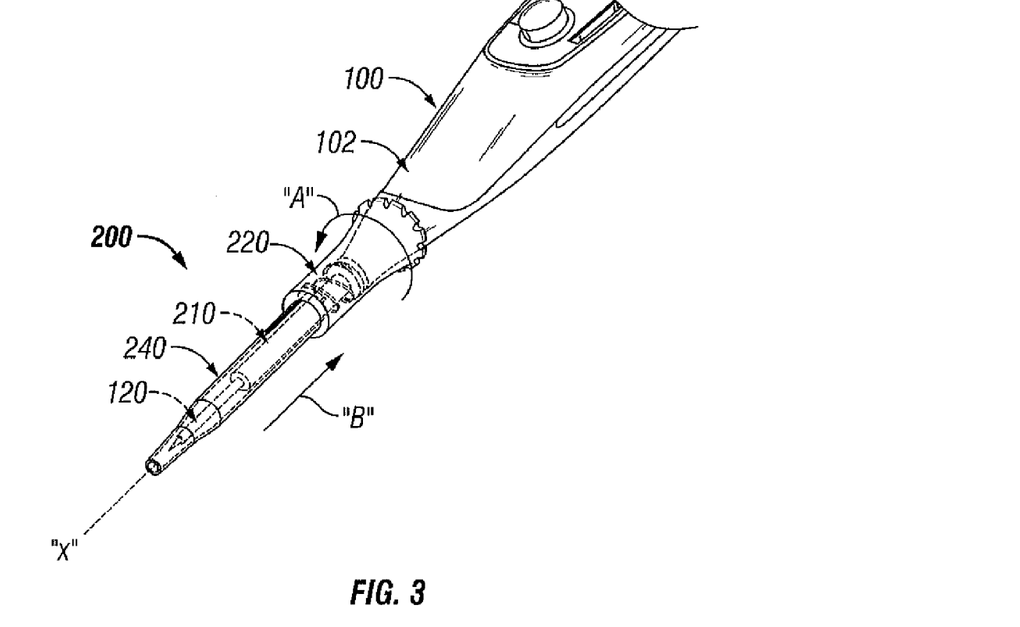
FIG. 3 is a perspective view of a distal end of an electrosurgical pencil of FIG. 1 illustrating the sheath system in a deployed or covering position.
Figure 4:
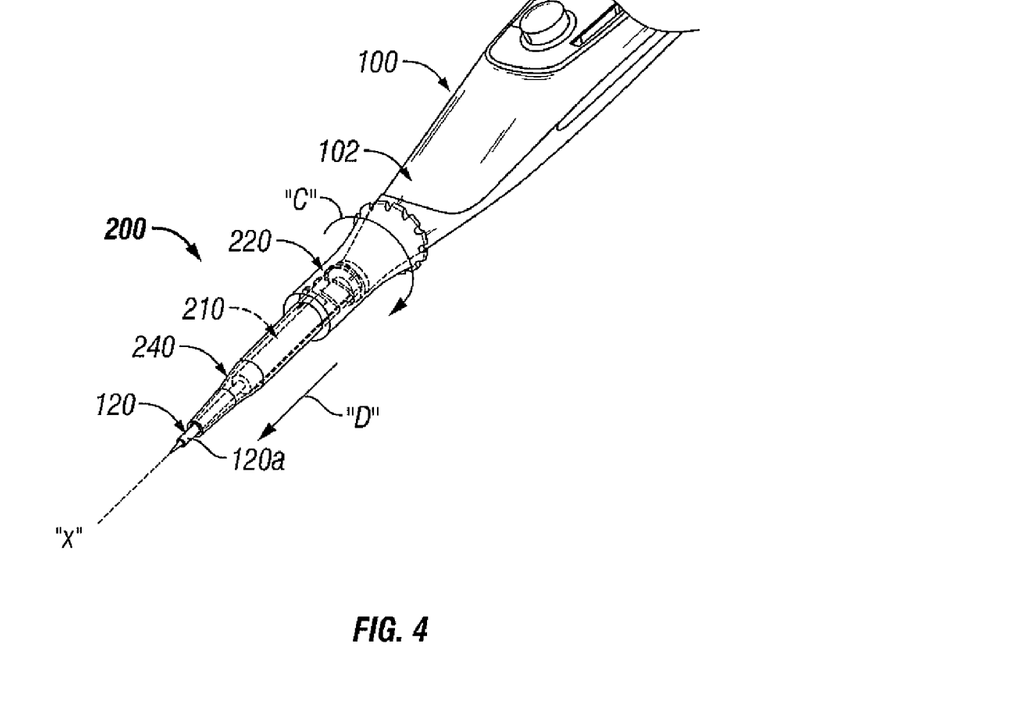
FIG. 4 is a perspective view of the distal end of the electrosurgical pencil of FIG. 1 illustrating the sheath system in a retracted or exposing condition.
Figure 5:
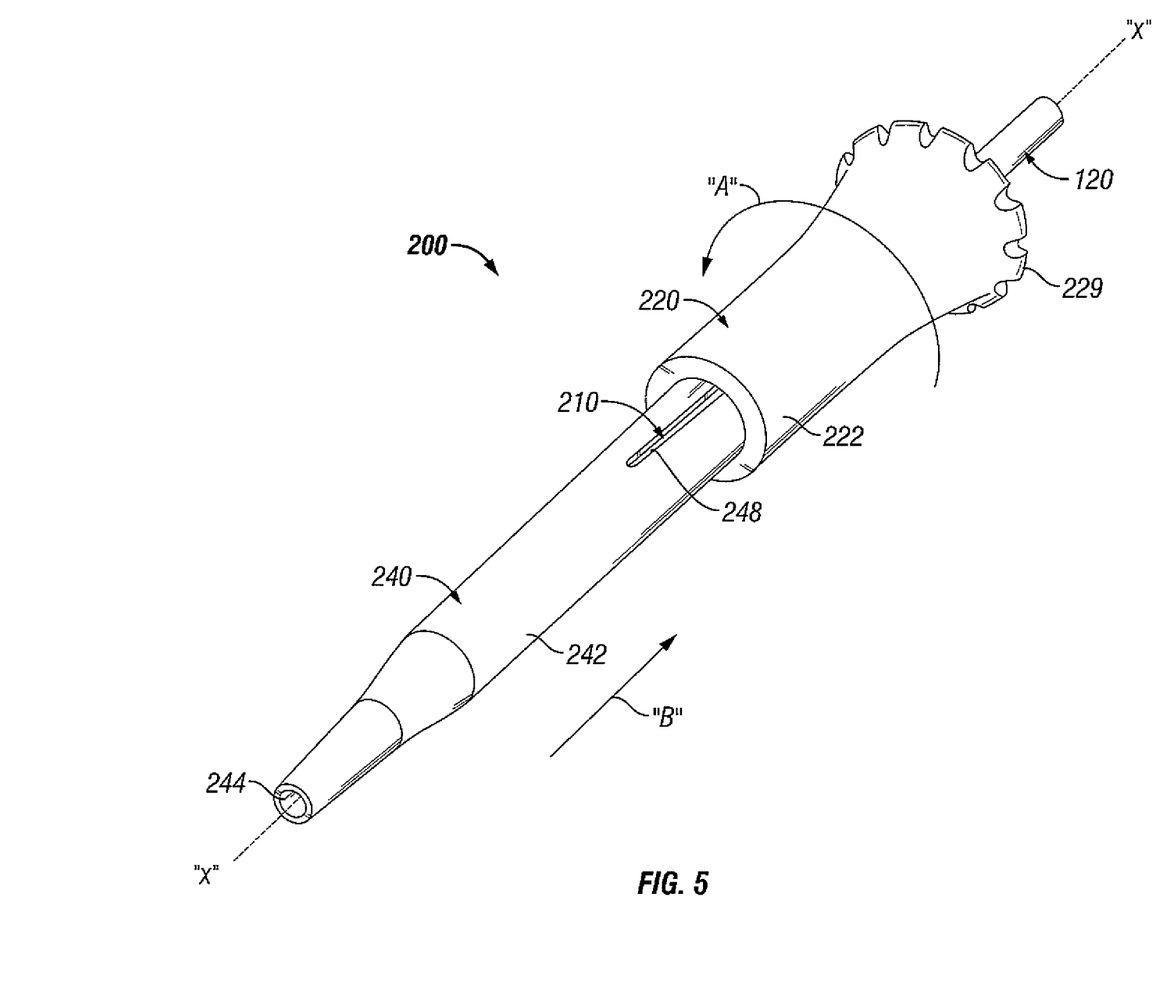
FIG. 5 is an enlarged perspective view of the sheath system of FIGS. 2-4, shown in the deployed or covering position.
Figure 6:
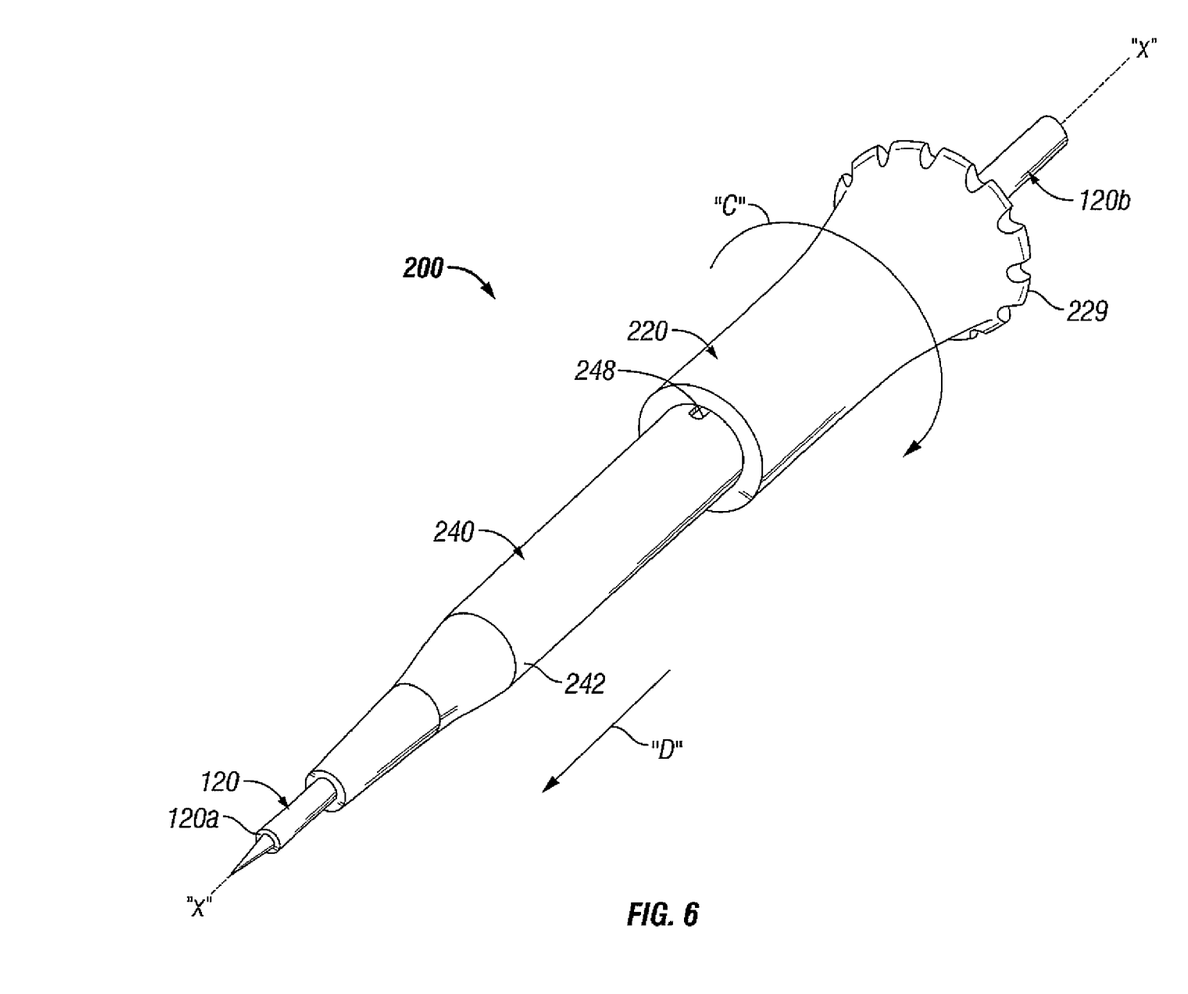
FIG. 6 is an enlarged perspective view of the sheath system of FIGS. 2-5, shown in the retracted or exposing condition.

Turning now to FIGS. 2-8, a sheath system for electrosurgical pencil 100, in accordance with an embodiment of the present disclosure, is generally designated as 200. Sheath system 200 is operatively supportable on a distal end of housing 102 of electrosurgical pencil 100. Sheath system 200 includes at least a first position in which sheath system 200 is deployed to completely cover electrocautery blade 120, as seen in FIGS. 3 and 5, and a second position in which sheath system 200 is retracted to expose electrocautery blade 120, as seen in FIGS. 4 and 6.

Figure 7:
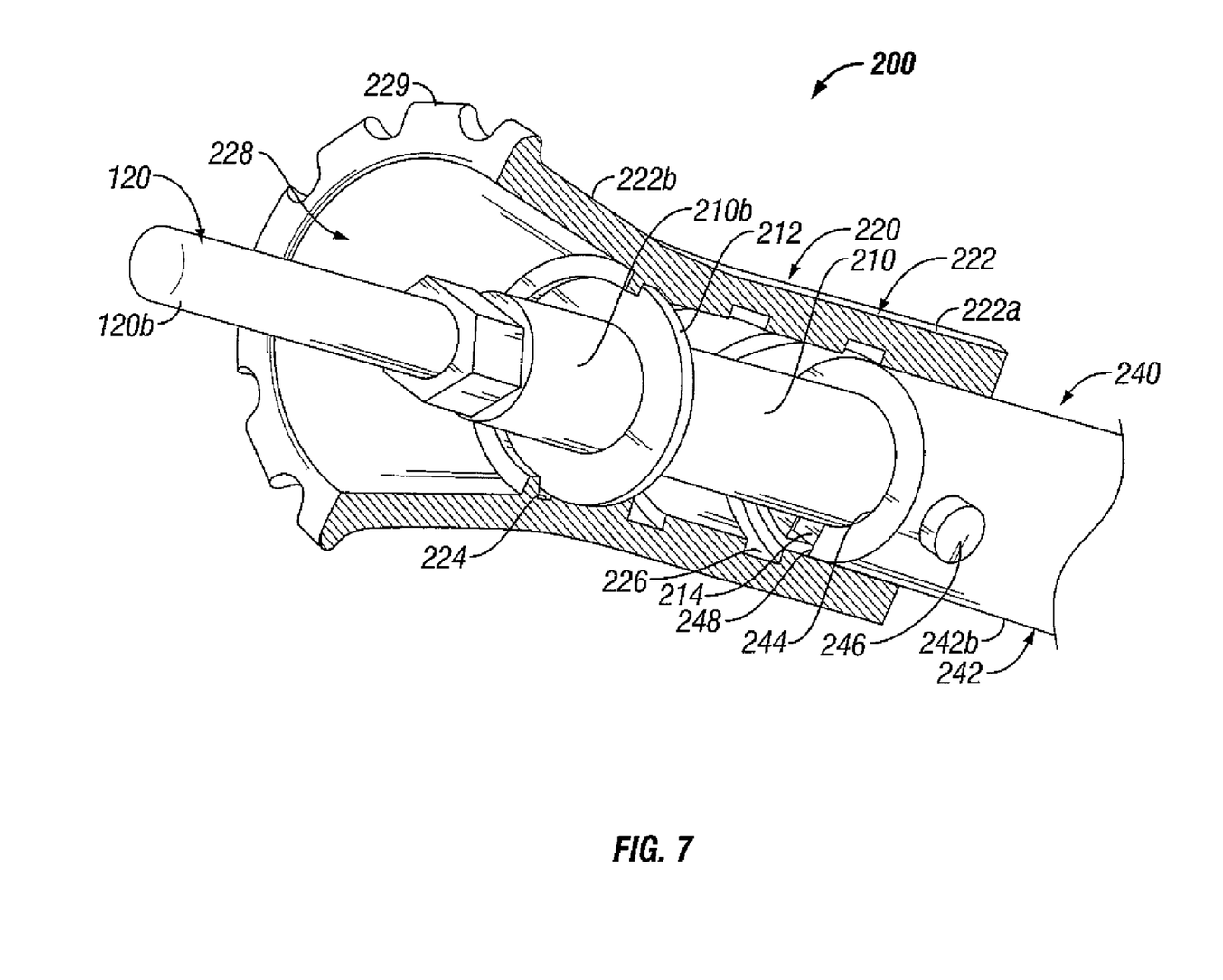
FIG. 7 is a rear, perspective, partial cross-sectional view of the sheath system of FIGS. 2-6.
Figure 8:
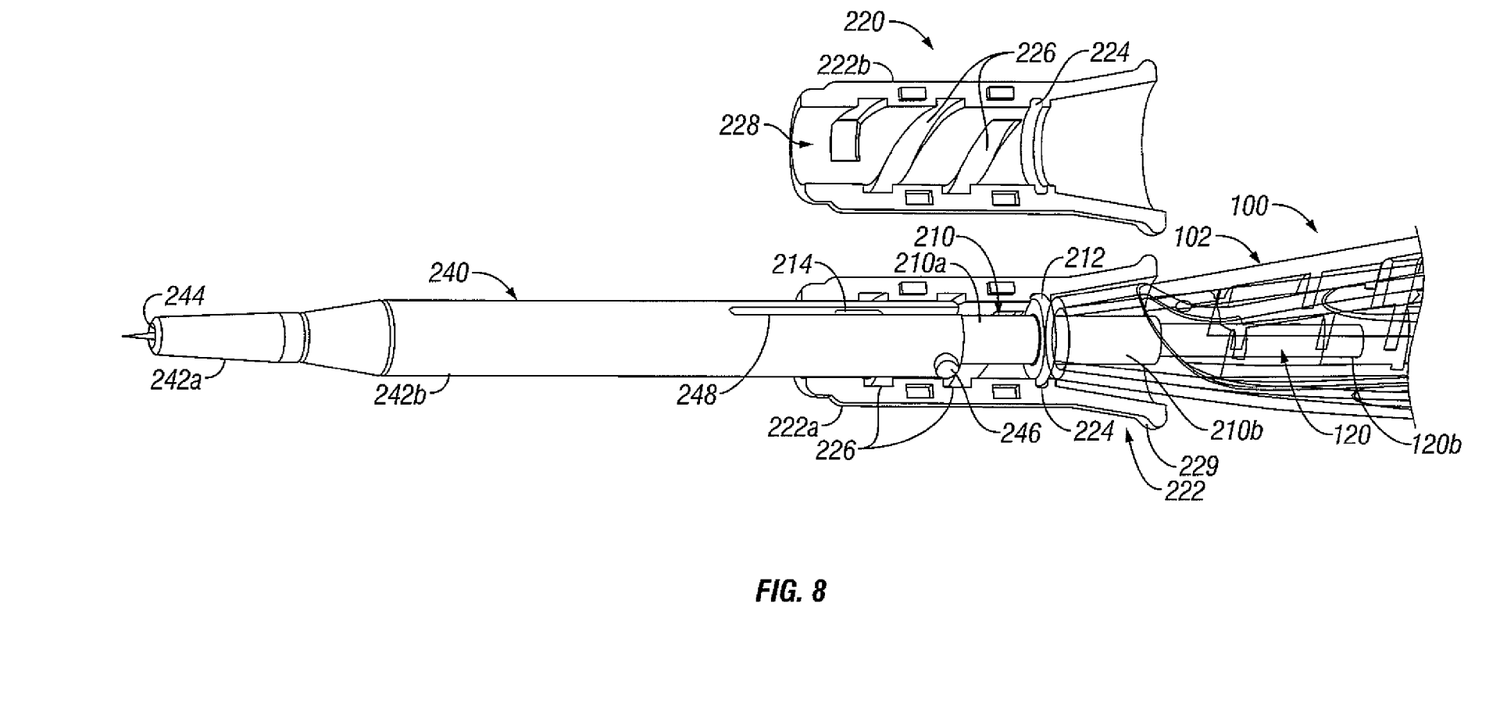
FIG. 8 is a perspective view of a distal end of an electrosurgical pencil of FIG. 1 illustrating the hub of the sheath system in a separated condition.

As seen in FIGS. 2, 7 and 8, sheath system 200 includes an elongate collar 210 configured and dimensioned to receive and support electrocautery blade 120. Desirably, collar 210 is dimensioned such that a distal end 120a of electrocautery blade 120 extends from a distal end 210a thereof, and a proximal end 120b of electrocautery blade 120 extends from a proximal end 210b thereof. Collar 210 includes an annular flange 212 extending therearound.

As seen in FIGS. 2-8, sheath system 200 further includes a hub 220 rotatably supportable at the distal end of housing 102; and a protective sheath 240 operatively connected to hub 220 in such a manner that as hub 220 is rotated, sheath 240 is displaced axially (i.e., either proximally or distally). As seen in FIG. 7, hub 220 includes an internal annular groove 224 formed in a body portion 222 thereof for rotatably receiving and supporting annular flange 212 of collar 210.

Body portion 222 of hub 220 includes a substantially cylindrical distal portion 222a and a flared or substantially frusto-conical proximal portion 222b. Flared proximal portion 222b is configured and dimensioned to approximate the taper and/or outer profile of the distal end of housing 102 of electrosurgical pencil 100. As mentioned above, collar 210 and, in turn, electrocautery blade 120, is rotatably supported in a lumen 228 defined by body portion 222 of hub 220.

As seen in FIGS. 7 and 8, hub 220 includes a helical groove 226 formed along an inner periphery thereof. Helical groove 226 is formed in an inner surface of distal portion 222a at a location distal to annular groove 224.

With continued reference to FIGS. 2-8, sheath 240 includes a body portion 242 defining a lumen 244 therethrough. Body portion 242 of sheath 240 desirably includes a tapered distal portion 242a, and a substantially cylindrical proximal portion 242b. Lumen 244 of sheath 240 is configured and dimensioned to operatively receive distal end 120a of electrocautery blade 120 and distal end 210a of collar 210 therein.

As seen in FIGS. 2, 7 and 8, sheath 240 includes at least one nub 246 projecting from an outer surface of body portion 242. A pair of diametrically opposed nubs 246 project from proximal portion 242b of body portion 242. Each nub 246 is configured and dimensioned to slidably seat within helical groove 226 formed in the inner surface of body portion 222 of hub 220. As will be described in greater detail below, nubs 246 cause sheath 240 to move distally and proximally as hub 220 is rotated in a clockwise or counter-clockwise direction.

Sheath 240 includes a longitudinally oriented elongate slot 248 formed in at least the proximal portion 242b of body portion 242. Elongate slot 248 is configured and dimensioned to slidably receive a stub 214 projecting from an outer surface of collar 210. As will be described in greater detail below, stub 214 of collar 210 prevents sheath 240 from rotating about a longitudinal axis as hub 220 is rotated.

Sheath 240 includes at least a first position in which sheath 240 is deployed to completely cover electrocautery blade 120, as seen in FIGS. 3 and 5, and at least a second position in which sheath 240 is retracted to expose at least the distal end 120a of electrocautery blade 120, as seen in FIGS. 4 and 6.

Each of collar 210, hub 220 and sheath 240 are fabricated from electrically non-conductive and/or insulative materials. In this manner, sheath system 200 does not electrically short electrocautery blade 120.

It is further desired for hub 220 to be provided with finger tabs or grips 229 formed around and along at least a portion of, preferably around and along substantially the entire length, a proximal edge of body portion 222. Grips 229 increase the users ability to rotate hub 220 about a longitudinal axis relative to housing 102 of electrosurgical pencil 100.

As seen in FIG. 2, collar 210, hub 220 and sheath 240 share a common longitudinal "X" axis. A central axis of electrocautery blade 120 is axially aligned with the longitudinal "X" axis. Additionally, a central axis of collar 210, a central axis of lumen 228 of hub 220, and a central axis of lumen 244 of sheath 240 are axially aligned with the longitudinal "X" axis. As will be described in greater detail below, hub 220 is rotatable about the longitudinal "X" axis and sheath 240 is translatable along the longitudinal "X" axis. In an embodiment, sheath 240 is concentrically aligned with hub 220.

When sheath system 200 is in the first or deployed condition, nubs 246 of sheath 240 at located at or near a distal end of helical groove 226 formed in hub 220. Additionally, stub 214 of collar 210 is located at or near a distal end of elongate slot 248 formed in proximal portion 242b of body portion 242. When sheath system 200 is in the second or retracted condition, nubs 246 of sheath 240 are located at or near a proximal of helical groove 226 formed in hub 220. Additionally, stub 214 of collar 210 is located at or near a proximal end of elongate slot 248 formed in proximal portion 242b of body portion 242.

Sheath system 200 is operatively connected to electrocautery blade 120 in such a manner that proximal end 120b of electrocautery blade 120 extends from hub 220. When electrocautery blade 120 is connected to electrosurgical pencil 100, sheath system 200 is necessarily operatively associated with electrosurgical pencil 100. In particular, when electrocautery blade 120 is operatively connected to electrosurgical pencil 100, proximal end 120b of electrocautery blade 120 enters an open distal end of housing 102 of electrosurgical pencil 100 and electrically engages and/or is connected to a blade receptacle (not shown) provided in electrosurgical pencil 100. A shaped portion 211b, preferably hex-shaped, of a proximal end 210b of collar 210 engages a complementary shaped recess (not shown) formed in housing 102 of electrosurgical pencil 100 to prevent rotation of blade 120 when properly coupled thereto. Additionally, a distal end of housing 102 of electrosurgical pencil 100 is positioned in lumen 228 of flared proximal portion 222b of body portion 222 of hub 220.

With continued reference to FIGS. 2-8, a method of operating sheath system 200 to expose and cover distal end 120a of electrocautery blade 120 is shown and described. Electrocautery blade 120 may be connected or coupled to and disconnected from electrosurgical pencil 100 when sheath 240 of sheath system 200 is in the deployed and/or extended condition. In this manner, accidental and/or inadvertent incidents of pricking are reduced and/or eliminated.

Initially, in order to expose distal end 120a of electrocautery blade 120, if sheath system 200 is in a first or deployed condition, wherein sheath 240 at least completely covers distal end 120a of electrocautery blade 120 as seen in FIGS. 3 and 5, hub 220 is rotated in a first direction about the longitudinal "X" axis, as indicated by arrow "A" of FIGS. 3 and 5. Since stub 248 of collar 210 is slidingly located in elongate slot 248 of collar 210, upon rotation of hub 220, in the direction of arrow "A", helical groove 226 of hub 220 engages nubs 246 and causes sheath 240 to withdraw or retract (i.e., move in a proximal direction as indicated by arrow "B" in FIGS. 3 and 5). With sheath 240 of sheath system 200 in a withdrawn or retracted condition, the user may operate electrosurgical pencil 100 in a standard or normal fashion.

Following use of electrosurgical pencil 100, sheath 240 of sheath system 200 is deployed in order to once again cover distal end 120a of electrocautery blade 120, in order to store electrosurgical pencil 100, to replace electrocautery blade 120 and/or to discard electrocautery blade 120.

In particular, if sheath system 200 is in a second or retracted condition, wherein sheath 240 at least partially uncovers distal end 120a of electrocautery blade 120 as seen in FIGS. 4 and 6, in order to recover distal end 120a of electrocautery blade 120, hub 220 is rotated in a second or opposite direction about the longitudinal "X" axis, as indicated by arrow "C" of FIGS. 4 and 6. Since stub 248 of collar 210 is slidingly located in elongate slot 248 of collar 210, upon rotation of hub 220, in the direction of arrow "C", helical groove 226 of hub 220 engages nubs 246 and causes sheath 240 to extend (i.e., move in a distal direction as indicated by arrow "D" in FIGS. 4 and 6). With sheath 240 of sheath system 200 in an extended condition, the user may remove electrocautery blade 120 and discard the same with the increased assurance that they will not be stuck or pricked by distal end 120a of electrocautery blade 120.

Helical groove 226 formed in body portion 222 of hub 220 may include a notch or catch-point (not shown) formed near a distal end thereof. The notch formed in helical groove 226 is configured and dimensioned to selectively receive a nub 246 of collar 210 when sheath 240 is in the fully deployed and/or extended condition. The notch formed in helical groove 226 desirably functions to prevent and/or reduce the likelihood of sheath 240 from sliding back (i.e., moving in a proximal direction) as a result of a force applied, in a proximal direction, to the distal end thereof.

In a further embodiment, hub 220 may include a ratchet or other anti-rotation feature (not shown) which functions to prevent sheath 240 from accidentally or unwantingly sliding proximally thereby exposing distal end 120*a* of electrocautery blade 120. This anti-rotation feature may only be disengageable when electrocautery blade 120 is connected to the distal end of housing 102 of electrosurgical pencil 100. The components of the anti-rotation feature desirably remain with electrocautery blade 120 when electrocautery blade 120 is removed from electrosurgical pencil 100 to provide continued safe handling of electrocautery blade 120.

In one embodiment, the anti-rotation feature is a flexible pawl (not shown) protruding inwardly from the inner surface of body portion 222 of hub 220 and inter-engaging a toothed ring (not shown) in electrocautery blade 120 or collar 210. In use, it is envisioned that when the distal end of housing 102 of electrosurgical pencil 100 enters the proximal end of lumen 228 of body portion of hub 220, housing 102 of electrosurgical pencil lifts the pawl and disengages the pawl from the toothed ring, allowing hub 220 to rotate.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments.

Those skilled in the art will envision other modifications within the scope and spirit of the claims appended hereto.

What is claimed is:

1. An electrocautery blade assembly configured for selective, removable connection to an electrosurgical device and being capable of transmitting electrosurgical energy, the electrocautery blade assembly comprising:

an electrocautery blade including a proximal end supportable in a housing of the electrosurgical device and a distal end extending distally from the housing, the electrocautery blade being selectively electrically connectable with a terminal of the electrosurgical device for connection to an electrosurgical generator;

a sheath system supporting the electrocautery blade therein, the sheath system being configured to selectively cover and expose the distal end of the electrocautery blade, the sheath system comprising:

a hub including a body portion defining a lumen therethrough;

a sheath including a body portion defining a lumen therethrough, the lumen of the sheath being configured and dimensioned to operatively receive the electrocautery blade therein, the sheath being translatably associated with the hub such that rotation of the hub in a first direction results in axial movement of the sheath in a first direction to expose the distal end of the electrocautery blade and rotation of the hub in a second direction, opposite to the first direction, results in axial movement of the sheath in a second direction to cover the distal end of the electrocautery blade; and a collar configured and dimensioned to support the electrocautery blade, wherein each of the distal end and the proximal end of the electrocautery blade extends from a respective distal and proximal end of the collar, wherein at least a portion of the collar is rotatably supported in the body portion of the hub, and wherein a portion of the collar is disposed in the lumen of the sheath.

2. The electrocautery blade assembly according to claim 1, wherein the proximal end of the collar is at least partially receivable in the housing of the electrocautery device.

3. The electrocautery blade assembly according to claim 1, wherein the body portion of the hub includes at least one helical groove formed in an inner surface thereof, and wherein the body portion of the sheath includes at least one nub extending from an outer surface thereof, wherein the nub is configured and dimensioned to slidably engage the groove of the hub.

4. The electrocautery blade assembly according to claim 3, wherein as the hub is rotated the nub of the sheath rides along the helical groove of the hub to translate the sheath in one of a distal and proximal direction.

5. The electrocautery blade assembly according to claim 4, wherein the collar includes an annular flange extending from an outer surface thereof, and wherein the hub includes an annular groove formed in an inner surface of the body portion, the annular groove of the hub being configured and dimensioned to slidably receive the annular flange of the collar.

6. The electrocautery blade assembly according to claim 5, wherein the body portion of the sheath includes an elongated slot formed therein, and wherein the collar includes a stub extending from the outer surface thereof, wherein the stub of the collar is configured and dimensioned to slidably engage the elongated slot formed in the body portion of the sheath.

7. The electrocautery blade assembly according to claim 6, wherein the inter-engagement of the stub of the collar in the elongate slot of the sheath prevents rotation of the sheath as the hub is rotated.

8. The electrocautery blade assembly according to claim 7, wherein at least a portion of each of the hub and the sheath is fabricated from non-conductive materials.

9. An electrocautery blade assembly for electrical connection to an electrosurgical device and, in turn, to an electrosurgical generator, the electrocautery blade assembly comprising:

an electrocautery blade including a proximal end configured for support in a housing of the electrosurgical device and a distal end configured to extend distally from the housing, the electrocautery blade being adapted for electrical connection to the electrosurgical generator;

a sheath system for selectively covering and exposing the distal end of the electrocautery blade, the sheath system including:

a hub including a body portion defining a lumen therethrough; and a sheath including a body portion defining a lumen therethrough, the lumen of the sheath being configured and dimensioned to operatively receive the electrocautery blade therein, the sheath being translatably associated with the hub such that rotation of the hub in a first direction results in axial movement of the sheath in a first direction to expose the distal end of the electrocautery blade and rotation of the hub in a second direction, opposite to the first direction, results in axial movement of the sheath in a second direction to cover the distal end of the electrocautery blade.

10. The electrocautery blade assembly according to claim 9, wherein the hub and the sheath are concentric with one another.

11. The electrocautery blade assembly according to claim 9, wherein the body portion of the hub includes at least one helical groove formed in an inner surface thereof, and wherein the body portion of the sheath includes at least one nub extending from an outer surface thereof, wherein the nub is configured and dimensioned to slidably engage the groove of the hub.

12. The electrocautery blade assembly according to claim 11, wherein as the hub is rotated, the nub of the sheath rides along the helical groove of the hub to translate the sheath in one of a distal and proximal direction.

13. The electrocautery blade assembly according to claim 9, the sheath system further comprising:
 a collar configured and dimensioned for support on the electrocautery blade, wherein each of the distal end and the proximal end of the electrocautery blade extends from a respective distal and proximal end of the collar, and wherein at least a portion of the collar is rotatably supported in the body portion of the hub and at least a portion of the collar is disposed in the lumen of the sheath.

14. The electrocautery blade assembly according to claim 13, wherein the collar includes an annular flange extending from an outer surface thereof and wherein the hub includes an annular groove formed in an inner surface of the body portion, the annular groove of the hub being configured and dimensioned to slidably receive the annular flange of the collar.

15. The electrocautery blade assembly according to claim 13, wherein the body portion of the sheath includes an elongated slot formed therein, and wherein the collar includes a stub extending from the outer surface thereof, wherein the stub of the collar is configured and dimensioned to slidably engage the elongated slot formed in the body portion of the sheath.

16. The electrocautery blade assembly according to claim 15, wherein the inter-engagement of the stub of the collar in the elongated slot of the sheath prevents the rotation of the sheath as the hub is rotated.

* * * * *